United States Patent [19]

Ochsner

[11] Patent Number: 4,657,700
[45] Date of Patent: Apr. 14, 1987

[54] FRAGRANCE COMPOSITIONS CONTAINING BENZYL ETHERS

[75] Inventor: Paul A. Ochsner, Geneva, Switzerland

[73] Assignee: Givaudan Corporation, Clifton, N.J.

[21] Appl. No.: 653,648

[22] Filed: Sep. 21, 1984

[30] Foreign Application Priority Data

Oct. 7, 1983 [CH] Switzerland .......... 5460/83
Jul. 12, 1984 [CH] Switzerland .......... 3387/84

[51] Int. Cl.$^4$ .............................. A61K 7/46
[52] U.S. Cl. ................. 252/522 R; 568/652; 560/144
[58] Field of Search ............ 252/522 R; 568/650, 568/651, 652; 560/144

[56] References Cited

U.S. PATENT DOCUMENTS

| | | | |
|---|---|---|---|
| 2,774,791 | 12/1956 | Alt .................. | 252/522 R |
| 3,010,995 | 11/1961 | Litvan et al. ........... | 568/652 |
| 3,947,603 | 3/1976 | Winter et al. ........... | 568/652 |
| 4,430,354 | 2/1984 | Boden et al. ........... | 252/522 R |

FOREIGN PATENT DOCUMENTS

| | | | |
|---|---|---|---|
| 57-188537 | 5/1981 | Japan ............ | 252/522 R |
| 57-9729 | 1/1982 | Japan ............ | 252/527 R |
| 57-82308 | 5/1982 | Japan ............ | 252/522 R |

OTHER PUBLICATIONS

W. G. Galetto and P. G. Hoffman, J. Agric. Food Chem. 26, (1978) 195–197.
E. Adler and S. Hernestam, Acta Chem. Scand. 9, (1955) 319, 330, 331.
S. Torii et al., J. Org. Chem. 44, (1979) 3305–3310.

Primary Examiner—James H. Reamer
Attorney, Agent, or Firm—Robert F. Tavares

[57] ABSTRACT

The invention concerns novel fragrance compositions containing benzyl ethers of the formula wherein:
$R^1$ represents an alkyl group containing one to three carbon atoms, and,
$R^2$ represents hydrogen or an alkanoyl group containing one to four carbon atoms.

Novel benzyl ethers of formula I also form part of the present invention.

21 Claims, No Drawings

FRAGRANCE COMPOSITIONS CONTAINING BENZYL ETHERS

The invention concerns novel fragrance compositions containing benzyl ethers of the formula

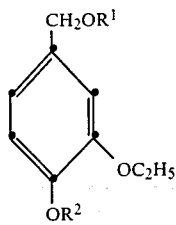

wherein:
$R^1$ represents an alkyl group containing one to three carbon atoms, and,
$R^2$ represents hydrogen or an alkanoyl group containing one to four carbon atoms.

The compounds of formula I possess organoleptic properties which make then excellently suitable as odorant substances.

Those benzyl ethers of formula I wherein $R^2$ is an alkanoyl group of one to four carbon atoms and the benzyl ether wherein $R^2$ is hydrogen and $R^1$ is an isopropyl group, are novel and also form part of the present invention.

DESCRIPTION OF THE PREFERRED EMBODIMENTS

The benzyl ethers of formula I are particularly distinguished by a combination of spicy, smoky-phenolic, vanilla-like olfactory notes. Flowery notes, especially those in the direction of carnation are also detectable. Table I below, describes the olfactory properties of benzyl ethers of formula I.

TABLE I

| $R^1$ | $R^2$ | Odor |
|---|---|---|
| CH₃ | H | resembling isoeugenol, vanilla, smoky-phenolic |
| C₂H₅ | H | spicy, resembling oranges, phenolic |
| n-C₃H₇ | H | musty, resembling methyleugenol, resembling vanilla |
| iso-C₃H₇ | H | spicy, resembling isoeugenol, smoky |
| CH₃ | CH₃CO | resembling vanillin, natural, a little phenolic, reminiscent of isoeugenol |
| C₂H₅ | CH₃CO | spicy, powdery note |
| HC(CH₃)₂ | CH₃CO | spicy, resembling vanilla beans, resembling carnations, |
| CH₃ | CH₃CH₂CO | flowery, spicy, buttery side-odour, resembling vanillin, |
| HC(CH₃)₂ | CH₃CH₂CO | spicy, vanilla-like, ethereal |

Preferred among the compounds disclosed in Table I are the phenolic ethers ($R^2$ is hydrogen) wherein $R^1$ is methyl (namely, 4-hydroxy-3-ethoxybenzyl methyl ether) and $R^1$ is isopropyl (namely, 4-hydroxy-3-ethoxybenzyl isopropyl ether). Both possess a powerful odor with very good tenacity. The isopropyl ether is especially preferred for its extremely powerful odor. Also preferred for its organoleptic properties is the alkanoyl ether of Table I wherein $R^1$ is isopropyl and $R^2$ is propionyl, namely, 4-propionyloxy-3-ethoxybenzyl isopropyl ether.

The prior art does not disclose the use of compounds of formula I as odorant substances. Vanillyl ethers of formula II wherein R represents an alkyl group of one to six carbons, have been disclosed as flavoring substances (Japanese Kokai No.: 82,308/82 and Japanese Kokai No.: 9729/82).

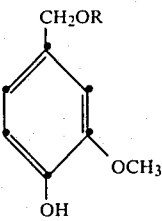

These ethers are reported as having a spicy taste and as being useful in dentrifice materials for their cooling effect. Those ethers in which R represents three to six carbon atoms are also reported to have properties that cause a burning feeling on the skin and to be useful as additives for harsh spices and as an active component in stretch plasters.

In comparison to the compounds of formula II the phenolic ethers of the present invention ($R^2$ in formula I is hydrogen), are found to be substantially more powerful with respect to odor. Compared under the same conditions they are on the average about three times stronger. This is especially apparent in a comparison of the bottom notes (dryout). The alkanoyl derivatives on comparison are found to have a weaker odor, but are distinguished by excellent tenacity.

On the basis of their olfactory properties the phenolic ethers of formula I ($R^2$ is hydrogen) are particularly suited as substitutes for isoeugenol, the use of which as a fragrance material has declined due to its skin irritating properties.

The ethers of formula I are suitable for the modification of an extremely wide range of known compositions, e.g., (a) flowery compositions, e.g., rose, lily, narcissus, in which e.g. the warm, spicy notes are to be intensified (e.g., for men's cologne), (b) fruity, lavender and chypre compositions (essence types, compositions of the feminine direction), (c) tobacco, woody and fougère compositions, (essence types of the masculine direction), and, (d) compositions with green notes, where in particular a desirable rounding off and harmonizing effect is produced.

As odorant substances the compounds I on the basis of their original notes described above are suitable, in particular, in combination with a series of natural and synthetic odorant substances such as e.g.

Natural products
such as angelica root oil, galbanum oil, vetiver oil, patchouli oil, sandalwood oil, mandarin oil, muscatsage, ylang-ylang oil, cedar oil, pine oil, lavender oil, bergamot oil, lemon oil, orange oil, coriander oil, oak moss, castoreum, ciste labdanum, calamus oil, geranium oil, jasmine absolute, rose oil, cassis absolute, narcissus absolute, vervain absolute, grapefruit extracts etc.

Aldehydes
such as $C_{10}$-, $C_{11}$-, $C_{14}$-aldehyde, hydroxycitronellal, cyclamen aldehyde, benzaldehyde, p-tert.-butyl-α-methyl-hydrocinnamaldehyde, citral, citronellal, 2,6-dimethyl-5-hepten-1-al, isovaleraldehyde, trans-2-hexenal, trans-2-octenal, n-octanal, n-nonanal, trans-2-cis-6-nonadienal, 2,4-decadienal, methyl nonyl acetaldehyde, 1,3-dimethyl-cyclohex-1-ene 4(and 5)-carboxaldehyde, and 3(and 4)-[4-Methyl-4-hydroxyamyl]-$\Delta^3$-cyclohexenecarboxaldehyde, etc.

Ketones
such as alpha-ionone, beta-ionone, methylionone, allylionone, acetanisole, 4-(para-hydroxyphenyl)-2-butanone, camphor, menthone, carvone, pulegone, p-methylacetophenone, methyl amyl ketone etc.

Acetals and ketals
such as phenylacetaldehyde dimethyl acetal, phenylacetaldehyde glycerine acetal, 2-methyl-1,3-dioxolan-2-ethyl acetate, capric aldehyde dimethyl acetal, Acetal R (mixed acetal of acetaldehyde with phenylethyl alcohol and n-propanol) etc.

Ethers
such as eugenol methyl ether, methyl 1-methylcyclododecyl ether, anethol, estragol, methylethyl saligenin etc.

Phenolic compounds
such as vanillin, eugenol, creosol, chavicol etc.

Alcohols
such as butanol, n-hexanol, cis-3-hexanol, trans-2-cis-6-nonadienol, cis-6-nonenol, linalool, geraniol, rhodinol, nerol, citronellol, nerolidol, farnesol, benzyl alcohol, phenylethyl alcohol, cinnamic alcohol, terpineol, 4-tert.-butylcyclohexanol etc.

Esters
such as ethyl formate, ethyl acetate, isoamyl acetate, t-butylcyclohexyl acetate, Myraldylacetat ™ (Givaudan), benzyl acetate, styrallyl acetate, ethyl α-methyl-phenylglycidate, maltyl isobutyrate, dimethylbenzylcarbinyl acetate and butyrate, linalyl acetate, isobutyl acetate, n-amyl butyrate, n-amyl valerate, ethyl palmitate, cinnamyl formate, terpenyl acetate, geranyl acetate, hexyl salicylate, linalyl anthranilate, amyl salicylate, methyl dihydrojasmonate, benzyl salicylate.

Lactones
such as γ-undecalactone, γ-decalactone, γ-nonalactone, δ-decalactone, δ-octalactone, coumarin etc.

Acids
such as geranic acid, citronellic acid, cinnamic acid, phenylacetic acid etc.

Sulfur-containing compounds
such as p-methane-8-thiol-3-one, dimethyl sulphide and other sulphides and disulphides etc.

Nitrogen-containing compounds
such as methyl anthranilate, indole, isobutylquinoline, various pyrazines, 5-methyl-heptan-3-one oxime, nitromusk etc.

Various additional components often used in perfumery
such as musk ketone, macrocyclic musk compounds such as Musk 174 ™ (Naarden) (12-oxahexadecanolide). Sandela ®️ (iso-camphyl-cyclohexanol), polycyclic musk compounds such as Fixolide ®️, (Givaudan (7-acetyl-1,1,3,4,4,6-hexamethyl-tetralin), and 1,3,4,6,7,8-Hexahydro-4,6,6,7,8,8-hexamethyl-cyclopenta-Y-2-benzopyran.

The compounds of formula I can be used in wide limits which, for example, can extend in compositions from 0.1 (detergents)–50% (alcoholic solutions). It will be appreciated that these values are, however, not limiting values, since the experienced perfumer can also produce effects with even lower concentrations or can synthesize novel complexes with even higher concentrations. The preferred concentrations range between 0.5 and 20%. The compositions manufactured with I can be used for all kinds of perfumed consumer goods (eau de cologne, eau de toilette, essences, lotions, creams, shampoos, soaps, salves, powders, deodorants, detergents, air fresheners etc).

The compounds I can accordingly be used in the manufacture of compositions and, as will be evident from the above compilation, a wide range of known odorant substances can be used. In the manufacture of such compositions the known odorant substances specified above can be used according to methods which are known to the perfumer such as e.g. according to W. A. Poucher, Perfumes, Cosmetics and Soaps 2, 7th Edition, Chapman and Hall, London, 1974.

The manufacture of vanillyl ethers has been described in the prior art (see e.g., Adler and Hernestam, Acta Chemica Scandinavica 9 (1955) 319–334, especially 331). By use of this known process the manufacture of 4-hydroxy-3-methoxybenzyl ethyl ether would require that an ethanolic HCl solution be added dropwise during 3 hours to an ice-cooled ethanolic vanillyl alcohol solution and the mixture be left to react at room temperature for 16 hours. In the course of the present investigations by contrast there has been developed a substantially simpler method for the manufacture of the ethers I from the corresponding benzyl alcohol: the ethylvanillyl alcohol is dissolved in the appropriate $C_{1-3}$-alkanol, sodium hydrogen sulphate is added thereto, the mixture is heated for a few minutes, conveniently to temperatures of ≦50° C., left to cool and worked up by neutralizing the sodium hydrogen sulphate and evaporating off the $C_{1-3}$-alkanol.

In this case the ratio 3-ethylvanillyl alcohol: $C_{1-3}$-alkanol conveniently amounts to at least 1:1, but the $C_{1-3}$-alkanol can also be present in excess.

The sodium hydrogen sulphate is conveniently added in about the same molar amount as the vanillyl alcohol, but the desired objective can also be achieved even with a deficiency, for example a 20% deficiency.

The alkanoyl derivatives

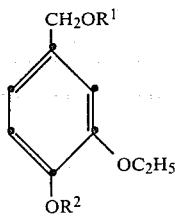

I'' wherein:
$R^1$ represents an alkyl group containing one to three carbon atoms and
$R^2$ represents an alkanoyl group containing one to four carbon atoms,
are obtained by esterifying a compound of the formula

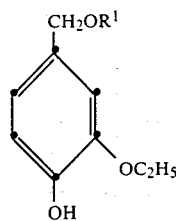

wherein $R^1$ has the above significance.

The esterification of the phenols I' is carried out in a manner known per se using the usual acylating agents, e.g. acyl halides or acid anhydrides. The procedure using the acid anhydrides is preferred. The esterification is conveniently carried out in the presence of mineral acids, e.g. $H_3PO_4$, or in the presence of the alkali metal salt of the corresponding carboxylic acid.

ILLUSTRATION OF THE PREFERRED EMBODIMENTS

Example 1

100 g of ethylvanillyl alcohol (4-hydroxy-3-ethoxybenzyl alcohol) are dissolved in 200 ml of methanol. The solution is treated with 10 g of sodium hydrogen sulphate and a knife tip of hydroquinone. The mixture is firstly heated to 50° C. for 2 minutes and left to cool again to room temperature. The methanolic solution is now poured into 85 ml of a saturated sodium hydrogen carbonate solution. The methyl alcohol is distilled off in vacuo, the residue is taken up in toluene, the organic solution is washed neutral with water and evaporated. The residue (95.5 g) is fractionally distilled. There are obtained 61.1 g of chemically and olfactorily pure 4-hydroxy-3-ethoxybenzyl methyl ether; b.p.=77° C./0.03 mmHg; $d_4^{20}=1.1084$; $n_D^{20}=1.529$. Yield: 56.3%.

The following ethers I are manufactured in an analogous manner, likewise starting from ethylvanillyl alcohol:

| | | |
|---|---|---|
| $R^1$ = ethyl | b.p. = 70° C./0.07 mmHg, | $d_4^{20}$ = 1.0756, $n_D^{20}$ = 1.521 |
| $R^1$ = n-propyl | b.p. = 101° C./0.2 mmHg, | $d_4^{20}$ = 1.0528, $n_D^{20}$ = 1.515 |
| $R^1$ = isopropyl | b.p. = 98° C./0.55 mmHg, | $d_4^{20}$ = 1.0489, $n_D^{20}$ = 1.512 |

All derivatives I are exceptionally heat and light stable.

Example 2

100 ml of dry toluene, 2.3 g of sodium propionate and 31.5 g (0.15 mol) of 4-hydroxy-3-ethoxybenzyl isopropyl ether are added to a round flask equipped with a stirrer, a thermometer, a condenser and a dropping funnel. 23 g (0.176 mol) of propionic anhydride are added dropwise at room temperature within 30 minutes while stirring. After the addition the reaction mixture is held at reflux temperature for 2 hours. After cooling the content of the flask is poured on to 100 g of ice, the organic layer is separated and washed three times with 50 ml of 10% sodium carbonate solution. After drying over sodium sulphate the solvent is evaporated and the residue (42 g) is distilled. Fractional distillation gives 35 g (yield: 87.5% of theory) of chemically pure propionic acid ester, 19 g thereof are olfactorily pure without further treatment; b.p.=104° C./0.1 mmHg; $d_4^{20}=1.0349$; $n_D^{20}=1.4877$. The remainder can be converted into olfactorily pure product by additional rectification.

The following alkanoyl derivatives are manufactured from the ethers I ($R^2$=H) in an analogous manner:

| | | |
|---|---|---|
| $R^1$ = methyl | $R^2$ = acetyl | b.p. = 91° C./0.17 mmHg, $d_4^{20}$ = 1.0997, $n_D^{20}$ = 1.5022 |
| $R^1$ = ethyl | $R^2$ = acetyl | b.p. = 96° C./0.16 mmHg, $d_4^{20}$ = 1.0715 $n_D^{20}$ = 1.4958 |
| $R^1$ = isopropyl | $R^2$ = acetyl | b.p. = 98° C./0.15 mmHg, $d_4^{20}$ = 1.0509 $n_D^{20}$ = 1.4911 |
| $R^1$ = methyl | $R^2$ = propionyl | b.p. = 89° C./0.05 mmHg, $d_4^{20}$ = 1.0783 $n_D^{20}$ = 1.4976 |

Example 3

A. Flowery base in the direction of carnation

| | Parts by weight |
|---|---|
| Dipropylene glycol | 100 |
| Terpineol | 260 |
| Hydroxycitronellal | 220 |
| Cinnamic alcohol - substitute | 120 |
| Phenylethyl alcohol | 100 |
| Cinnamyl formate | 20 |
| Linalool | 15 |
| Terpenyl acetate | 10 |
| Musk ketone | 10 |
| Geranyl acetate | 10 |
| Jasmine synthetic | 10 |
| Eugenol | 5 |
| Indole 10% in dipropylene glycol (DPG) | 5 |
| $C_{10}$—aldehyde 10% in DPG | 5 |
| p-Methylacetophenone | 5 |
| Undecalactone | 5 |
| | 900 |

By the addition of 100 parts of the methyl derivative I ($R^2$=H) the base takes on a very pleasant powdery-flowery character with a slight green note in the direction of carnation. An analogous effect can be produced by the addition of 100 parts of isoeugenol. The addition of 100 parts of the isopropyl derivative I ($R^2$=H) confers to the base a pleasant sweetness and volume; by the addition the jasmine-lilac complex is enveloped in a powdery-spicy note, in other words: the typical carnation note results. On the other hand, if 100 parts of 4-hydroxy-3-methoxybenzyl methyl ether or 100 parts of 4-hydroxy-3-methoxybenzyl isopropyl ether are added to the above base of generally flowery direction, the base becomes unbalanced from the point of view of odour. The olfactory note receives a hard character; the flowery element is completely suppressed.

B. Carnation base

| | Parts by weight |
|---|---|
| Eugenol | 250 |
| Phenylethyl alcohol | 100 |
| Dipropylene glycol | 70 |
| Terpineol | 60 |
| Ylang-ylang oil | 50 |
| Benzyl salicylate | 50 |
| α-Ionone | 30 |
| Hydroxycitronellal | 30 |
| Amyl salicylate | 20 |
| Rhodinol | 80 |

-continued

| | Parts by weight |
|---|---|
| Phenylacetaldehyde | 10 |
| | 750 |

By the addition of 250 parts of the methyl derivative I ($R^2=H$) to the above flowery base this base becomes very pleasantly enveloped. A very soft powdery carnation odour develops. Also, the addition of 250 parts of the isopropyl derivative I ($R^2=H$) brings about in the original base a very pleasant powdery and rounded-off olfactory note in the direction of carnation. Also, by the addition of 250 parts of isoeugenol the flowery base receives its typical carnation character with the somewhat sharp green note. On the other hand, if 250 parts of 4-hydroxy-3-methoxybenzyl methyl ether or 4-hydroxy-3-methoxybenzyl isopropyl ether are added, then the base becomes unbalanced from the point of view of odour. It now becomes flat and the eugenol dominates, so that a terpene-like impression results.

Example 4

This Example demonstrates how, in every respect conventional, bases can be improved in an unexpected and desirable manner by the addition of compounds I. In each case the additions amount to 10 parts. On the other hand, an improvement by means of isoeugenol could not be observed here in any instance.
The additives referred to are:

| | |
|---|---|
| 4-Hydroxy-3-ethoxybenzyl methyl ether | (A) |
| 4-Hydroxy-3-ethoxybenzyl isopropyl ether | (B) |
| 4-Propionyloxy-3-ethoxybenzyl isopropyl ether | (C) |
| 4-Acetoxy-3-ethoxybenzyl methyl ether | (D) |

A. Perfumery base in the direction of rose

| | Parts by weight |
|---|---|
| Phenylethyl alcohol | 300 |
| Geraniol extra | 300 |
| Jasmine synthetic | 240 |
| Citronellol | 100 |
| α-Ionone | 40 |
| $C_{10}$—aldehyde 10% in dipropylene glycol | 5 |
| $C_{11}$—aldehyde 10% in dipropylene glycol | 5 |
| | 990 |

By the addition of 10 parts of A there results a very pleasant powdery and spicy rose which tends in the direction of light rose.

An addition of 10 parts of C confers very much more warmth and fullness to the base. A very round dark rose results.

By the addition of 10 parts of B the base becomes very powdery, very sweet and heavy.

B. Perfumery base in the direction of narcissus

| | Parts by weight |
|---|---|
| Hydroxycitronellal | 400 |
| Phenylethyl alcohol | 400 |
| Aubepine (p-anisaldehyde ex anethol) | 50 |
| p-Cresyl acetate 10% DPG | 30 |
| Ylang-ylang oil | 20 |
| Dipropylene glycol | 90 |
| | 990 |

10 parts of A bring the base from the direction of narcissus into the direction of lilac. The base is, however, much warmer and more powdery, the aubepine character is strongly underlined.

With 10 parts of D the narcissus note of the base becomes substantially stronger and more typical.

Also, by the addition of 10 parts of C the base becomes more flowery, moreover softer and very well rounded-off.

C. Perfumery base in the direction of chypre

| | Parts by weight |
|---|---|
| Raldeine ® (Givaudan) (mixture of methyl ionones) | 200 |
| Musk ketone | 100 |
| Phenylethyl alcohol | 80 |
| Linalyl acetate | 70 |
| Tree moss absolute | 50 |
| Vetivenyl acetate | 50 |
| Methyl dihydrojasmonate | 50 |
| α-Hexylcinnamaldehyde | 50 |
| Patchouli oil | 30 |
| Citronellol ex geranium oil | 30 |
| Eugenol | 30 |
| Sandela ® (Givaudan) (isocamphyl-cyclohexanol) | 30 |
| Cedarwood oil | 30 |
| Styrallyl acetate | 20 |
| Galbanum oil | 10 |
| Neroli oil | 10 |
| Castoreum oil 10% DPG | 10 |
| Isobutylquinoline 10% DPG | 10 |
| Armoise oil | 10 |
| $C_{11}$—aldehyde 10% in DPG | 10 |
| Citral | 5 |
| Undecalactone | 5 |
| Cistus oil | 5 |
| Dipropylene glycol | 95 |
| | 990 |

An addition of 10 parts of A produces in the chypre base a very pleasant powdery, warm note which is rounded off very well.

An extremely good rounding-off is likewise achieved by addition of 10 parts of B. The base is much softer, the complex neroli-musk ketone is harmoniously underlined; very well suited for feminine lines.

On the other hand, the addition of 10 parts of C underlines the woody, somewhat spicy note of the complex vetiver-patchouli-cedarwood; very well suited for masculine lines.

D. Perfumery base in the direction of fougere

| | Parts by weight |
|---|---|
| Tree moss absolute | 60 |
| Lavender oil French | 200 |
| Linalyl acetate | 150 |
| Coumarin | 50 |
| Patchouli oil | 30 |
| Citronellol ex geranium oil ("rhodinol") | 30 |
| Methyl dihydrojasmonate | 30 |
| Musk ketone | 30 |
| Vetivenyl acetate | 30 |
| Geranium Bourbon synthetic | 30 |
| Amyl salicylate | 20 |
| Sandela ® (Givaudan) (isocamphyl-cyclohexanol) | 20 |
| Linalool | 20 |
| Benzyl acetate | 15 |
| Ylang-ylang oil | 15 |
| Eugenol | 15 |
| Thyme oil | 5 |
| Dipropylene glycol | 240 |

-continued

| | Parts by weight |
|---|---|
| | 990 |

If 10 parts of A are added to the above fougere base, then the spicy coumarin aspect is underlined very well.

However, if D is added thereto, then the base becomes much more woody. The complex patchouli-Sandela now becomes rounded-off very advantageously.

If, however, C is added to the base, this immediately becomes very much warmer. The somewhat hard salicylate-lavender note now becomes pleasantly rounded-off in that it combines with the flowery components of the rhodinol/methyl dihydrojasmonate.

E. Fresh-green base

| | Parts by weight |
|---|---|
| Linalyl acetate | 200 |
| Linalool synthetic | 200 |
| Lavender ess. France | 200 |
| Landenol (mixture of tetrahydro-linalool, tetrahydromyrcenol,) 3,7-dimethyl-4-octen-3-ol, 2,6-dimethyl-3-octen-2-ol) | 150 |
| Rosemary oil | 50 |
| Peppermint oil Brazilian | 20 |
| Sage oil French | 20 |
| Ambersage ® (Givaudan) (4,7-dihydro-2-isopentyl-2-methyl-1,3-dioxepin) | 20 |
| Eucalyptol | 20 |
| Pine needle oil | 10 |
| Methyl salicylate 10% DPG | 5 |
| Eugenol | 5 |
| Dione (Givaudan) (2-[3,3,5-trimethyl-cyclohexylacetyl]-cyclopentanone) | 5 |
| Galbanum oil (natural) | 5 |
| Dipropylene glycol | 80 |
| | 990 |

By the addition of 10 parts of B the above base receives a very warm, powdery sweet character, the somewhat hard effect of methyl salicylate and galbanum now becomes very advantageously enveloped.

An addition of 10 parts of C envelopes the base very pleasantly; the gain in volume and diffusion enables it to be used for compositions in the direction of feminine lines.

I claim:

1. A fragrance composition comprising an olfactorily effective amount of a compound of the formula

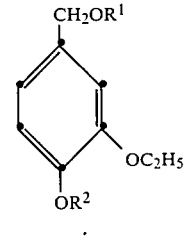

wherein:
$R^1$ represents an alkyl group containing one to three carbon atoms, and
$R^2$ represents hydrogen or an alkanoyl group containing one to four carbon atoms,
and at least one other olfactory agent.

2. A composition according to claim 1 wherein $R^2$ is hydrogen.

3. A composition according to claim 2 wherein the compound is 4-hydroxy-3-ethoxybenzyl methyl ether.

4. A composition according to claim 2 wherein the compound is 4-hydroxy-3-ethoxybenzyl isopropyl ether.

5. A composition according to claim 1 wherein $R^2$ is an alkanoyl group containing one to four carbon atoms.

6. A composition according to claim 5 wherein the compound is 4-acetoxy-3-ethoxybenzyl methyl ether.

7. A composition according to claim 5 wherein the compound is 4-propionyloxy-3-ethoxybenzyl isopropyl ether.

8. A method for improving the odor of a fragrance composition which comprises adding thereto an olfactorily effective amount of a compound of the formula

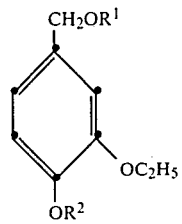

wherein:
$R^1$ represents an alkyl group containing one to three carbon atoms, and,
$R^2$ represents hydrogen or an alkanoyl group containing one to four carbon atoms.

9. A method according to claim 8 wherein $R^2$ is hydrogen.

10. A method according to claim 9 wherein the compound is 4-hydroxy-3-ethoxybenzyl methyl ether.

11. A method according to claim 9 wherein the compound is 4-hydroxy-3-ethoxybenzyl isopropyl ether.

12. A method according to claim 8 wherein $R^2$ is an alkanoyl group containing one to four carbon atoms.

13. A method according to claim 12 wherein the compound is 4-acetoxy-3-ethoxybenzyl methyl ether.

14. A method according to claim 12 wherein the compound is 4-propionyloxy-3-ethoxybenzyl isopropyl ether.

15. A compound of the formula

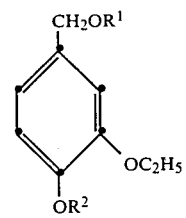

wherein:
$R^1$ represents an alkyl group containing one to three carbon atoms, and,
$R^2$ represents an alkanoyl group containing one to four carbon atoms.

16. A compound according to claim 15 which is 4-acetoxy-3-ethoxybenzyl methyl ether.

17. A compound according to claim 15 which is 4-propionyloxy-3-ethoxybenzyl methyl ether.

18. A compound according to claim 15 which is 4-acetoxy-3-ethoxybenzyl ethyl ether.

19. A compound according to claim 15 which is 4-acetoxy-3-ethoxybenzyl isopropyl ether.

20. A compound according to claim 15 which is 4-propionyloxy-3-ethoxybenzyl isopropyl ether.

21. 4-Hydroxy-3-ethoxybenzyl isopropyl ether.

* * * * *